United States Patent [19]

Grable

[11] Patent Number: 4,898,172

[45] Date of Patent: Feb. 6, 1990

[54] OPTICAL LIGHT PROBE

[76] Inventor: Richard J. Grable, 7400 SW. 13th St., Plantation, Fla. 33317

[21] Appl. No.: 853,394

[22] Filed: Apr. 18, 1986

[51] Int. Cl.[4] .............................................. A61F 7/00
[52] U.S. Cl. ..................................... 128/397; 128/23; 128/665
[58] Field of Search ............... 128/23, 303.1, 395–398, 128/633, 635

[56] References Cited

U.S. PATENT DOCUMENTS

| | | | |
|---|---|---|---|
| 1,662,150 | 3/1928 | Kerr | 128/397 |
| 1,706,161 | 3/1929 | Hollnagel | 128/23 |
| 1,800,277 | 4/1931 | Boerstler | 128/23 |
| 1,965,865 | 7/1934 | Thompson | 128/23 |
| 2,227,422 | 1/1941 | Boerstler | 128/397 |
| 3,195,536 | 7/1965 | Hovnanian et al. | 128/23 |
| 3,299,884 | 1/1967 | Moore et al. | 128/23 |
| 4,212,306 | 7/1980 | Mahmud | 128/665 |
| 4,233,493 | 11/1980 | Nath | 128/303.1 |
| 4,286,602 | 9/1981 | Guy | 128/665 |
| 4,312,357 | 1/1982 | Andersson et al. | 128/665 |

FOREIGN PATENT DOCUMENTS

273473  7/1927  United Kingdom .................. 128/23

*Primary Examiner*—Max Hindenburg
*Attorney, Agent, or Firm*—Shlesinger & Myers

[57] ABSTRACT

A hand held light source probe for use with a transillumination apparatus for tumor detection having a housing with a handle, light source, light skill and air circulating means.

3 Claims, 1 Drawing Sheet

OPTICAL LIGHT PROBE

BACKGROUND OF THE INVENTION

Transillumination apparatus for tumor detection in female human breasts generally requires a high intensity light source in a hand held probe. That portion of the probe to be engaged by the operator's hand must be cool enough to permit use for substantial time periods and the breast contacting potion of the probe must be substantially uniformly lighted with no focal spots of the light source which could burn the breast tissue.

BRIEF DESCRIPTION OF THE INVENTION

The probe of the present invention has a housing which includes a heat insulating handle portion enclosing an air cooled high intensity light source. A light pipe has a proximal plane surface end within the housing and terminates at its distal end following a curved section in a second plane surface spaced from the housing and lying at substantially 90° to the proximal surface. A light shield having substantially less area than the proximal end of the pipe is positioned between the light source and the pipe to positively prevent random focal points of light on the distal end of the pipe. The handle portion also includes a fan means positioned on that side of the light source remote from the light pipe to provide a cooling circulation of air over the exterior of the light source and the interior of the housing.

DETAILED DESCRIPTION

Figure 1:
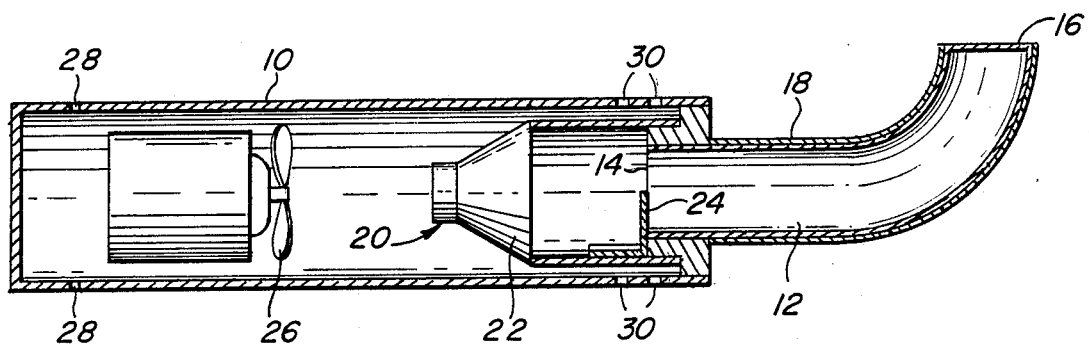
FIG. 1 is a side elevation partially in section of the probe.

Referring to the drawings, the probe includes a handle portion 10 having a light pipe 12 extending from one end thereof. The pipe which is formed of LUCITE or the like has a proximal face 14 within the housing and a distal face 16 for contact with human tissue. The pipe is curved through a substantially 90° bend which facilitates positioning of the probe by the operator. The exterior side wall of the pipe is completely covered with a bright aluminum foil 18 so that all light projected into the pipe is retained and appears only at the distal end.

Figure 2:
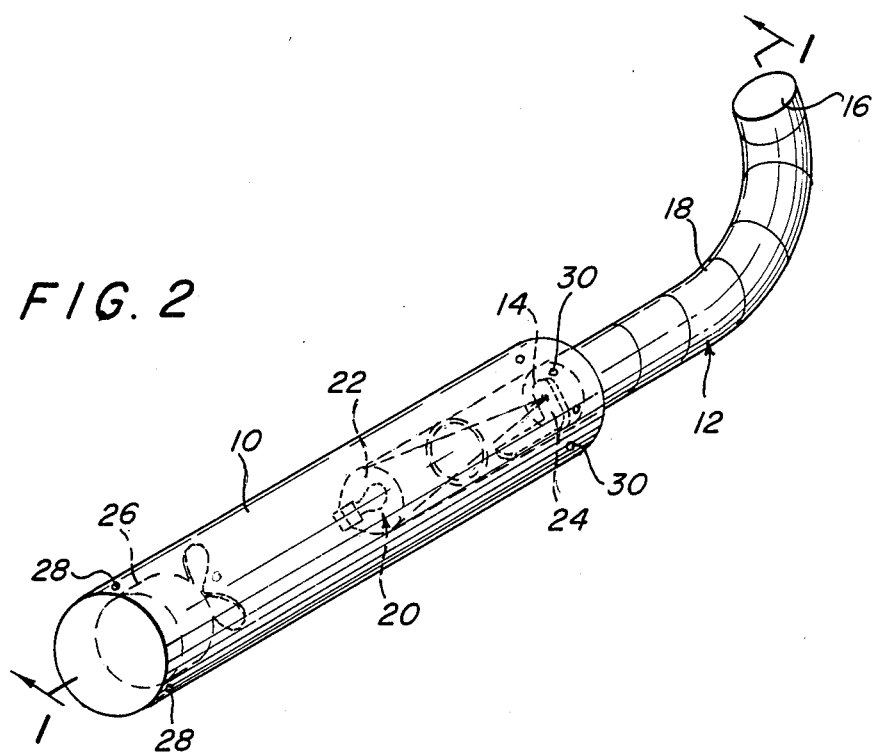
FIG. 2 is a perspective view of FIG. 1.

A light source 20 to illuminate the proximal face of the light pipe is mounted within the housing and is preferably an incandescent lamp of the projector type incorporating a reflector 22 which will focus the light from the filament at a fixed distance. In order to positively prevent the occurrence of random focal spots at the distal face of the light pipe, which could otherwise occur due to internal reflection from the foil wrap, a light shield 24 is positioned between the light source an the pipe. As shown most clearly in FIG. 2, the shield is of substantially less area than the proximal surface of the pipe.

Since light sources of this type generate considerable heat, a cooling means must be provided as shown by the fan 26 which will positively circulate air from openings 28 in the rear of the housing over the light source and the interior of the housing and then outwardly of the housing through openings 30.

The light source 20 is rigidly mounted in any convenient manner within the housing at a fixed distance from the light pipe.

The handle portion of the probe may be formed from a section of cylindrical PVC pipe and coated on its exterior surface by spray painting with aluminum paint to block the transmission of light and infrared energy.

While a preferred embodiment has been herein shown and described, Applicant claims the benefit of a full range of equivalents within the scope of the appended claims.

I claim:

1. A hand held light source probe for use with transillumination apparatus for tumor detection in human female breasts comprising:
   a housing including a hollow heat insulating handle portions;
   a pipe having proximal and distal ends extending longitudinally from one end of said housing, curing through substantially 90°, and terminating at its distal end in a plane surface;
   a high intensity incandenscent reflectorized light source positioned in said housing to illuminate the proximal end of said light pipe;
   a fixed opaque light shield of substantially less area than the proximal end of said light pipe so positioned in the projected light path of said bulb between said bulb and said pipe as to positively prevent the presence of a focal spot from said source on the distal end of said light pipe; and
   means for positively circulating cooling air through said housing and over the outer surface of said bulb.

2. The combination as defined by claim 1 including a highly reflective coating completely covering the outer surface of said light pipe.

3. The combination as defined by claim 1 in which said housing is a PVC cylinder having an external coating of aluminum spray paint.

* * * * *